(12) United States Patent
Hall et al.

(10) Patent No.: US 10,163,614 B1
(45) Date of Patent: Dec. 25, 2018

(54) ION MODULATOR FOR CHARACTERIZING LARGER BIOMOLECULES IN A DIFFERENTIAL MOBILITY SPECTROMETER

(71) Applicants: David R. Hall, Provo, UT (US); Dan Allen, Springville, UT (US); Joe Fox, Spanish Fork, UT (US)

(72) Inventors: David R. Hall, Provo, UT (US); Dan Allen, Springville, UT (US); Joe Fox, Spanish Fork, UT (US)

(73) Assignee: Hall Labs, LLC, Provo, UT (US)

( * ) Notice: Subject to any disclaimer, the term of this patent is extended or adjusted under 35 U.S.C. 154(b) by 0 days.

(21) Appl. No.: 15/632,636

(22) Filed: Jun. 26, 2017

(51) Int. Cl.
*H01J 49/06* (2006.01)
*H01J 49/40* (2006.01)
*H01J 49/04* (2006.01)
*G01N 27/62* (2006.01)

(52) U.S. Cl.
CPC ............ *H01J 49/06* (2013.01); *G01N 27/624* (2013.01); *H01J 49/0422* (2013.01); *H01J 49/40* (2013.01)

(58) Field of Classification Search
CPC .... H01J 49/0422; H01J 49/06; G01N 27/622; G01N 27/624
See application file for complete search history.

(56) References Cited

U.S. PATENT DOCUMENTS

2013/0284916 A1* 10/2013 Sato ..................... G01N 27/624
250/288
2016/0133451 A1* 5/2016 Vidal-de-Miguel ........................
G01N 27/622
250/423 R

* cited by examiner

*Primary Examiner* — Eliza Osenbaugh-Stewart

(57) ABSTRACT

The tandem differential mobility spectrometer (DMS)-ion modulator instrument provides improved resolution relative to traditional DMS for molecules with larger masses. The instrument includes an ion-bunching electrode with an AC field synchronized to the transit time of the ion flow which is positioned downstream of a DMS. The ion bunching electrode produces a mobility-dependent modulation of the ion current. The ratio of AC to DC current provides a measure of the mobility of a large ion, even if it has little differential mobility, thereby extending the useful range of mobility characterization of a DMS system. The instrument is more compact than a larger traditional ion mobility spectrometer and does not require high voltages or high frequencies. Modulation before DMS separation or between tandem DMS separations produces a variable range of analyte and reactant ion densities as well as spatially separating negative and positive ions to reduce ion recombination.

18 Claims, 11 Drawing Sheets

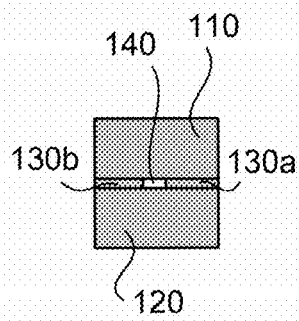
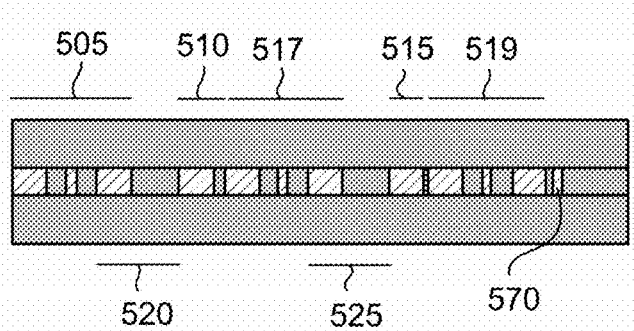
FIG. 5A
FIG. 5B
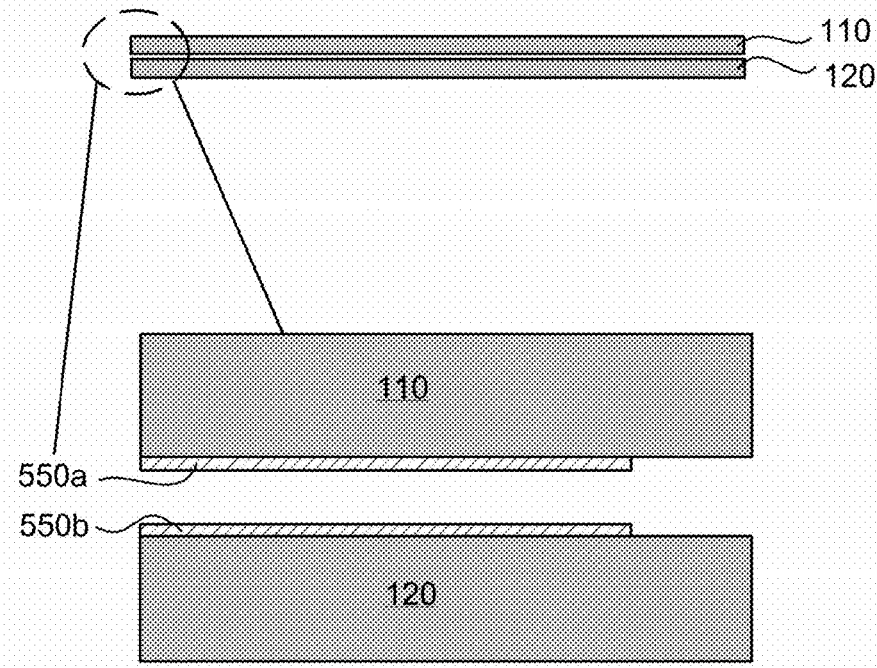
FIG. 5C

ION MODULATOR FOR CHARACTERIZING LARGER BIOMOLECULES IN A DIFFERENTIAL MOBILITY SPECTROMETER

BACKGROUND

Field of the Invention

This disclosure relates to analytical machinery and the identification and separation of molecules.

Background of the Invention

Differential mobility spectrometers (hereinafter, "DMS"), also called field asymmetric ion mobility spectrometers (FAIMS) operate by applying an asymmetric transverse alternating current field to a stream of ions moving in a carrier gas, for example, air. The asymmetric field has a high field portion which is on for a short duration, and a low field portion of opposite polarity which is on for a longer duration. Unlike vacuum ion sorting methods which operate in the ballistic flow regime (no atom collisions), for example, mass spectrometers, ion mobility spectrometers operate in the viscous flow regime (e.g. atmospheric pressure). This means that molecules are rapidly colliding and ions in an electric field (E) experience a terminal velocity (v) that depends on their collision cross section, which is related to their mobility (K) in the following way: $v=K*E$.

Mobility may be a function of electric field $K(E)=K0*(1+\alpha E)$. Under high field conditions, molecules experience high energy collisions, collisional orienting, and lose adducted molecules such as water, which tends to increase their mobility. Therefore, molecules with larger a (ion mobility function) tend to travel further in the high field portion of the cycle than the low field portion of the cycle and tend to drift toward one of the electrodes. A counter voltage (hereinafter, "CV") applies a direct current field component to re-center an analyte with a particular differential mobility. By sweeping CV, a differential mobility spectrum may be obtained by an ion detector downstream of the DMS. Notably, ions of opposite polarity can be measured independently. By selecting a particular CV, a DMS can function as an ion differential mobility filter for downstream analyzers, including mass spectrometers.

However, larger molecules have small differential ion-mobility function (hereinafter, "α"), and can experience drag, so large molecules are not well sorted or differentiated by a DMS. This limits the practical use of the DMS technique to small molecules. Traditional ion mobility spectrometer (IMS) systems, including a drift tube IMS, do not have this limitation because they measure mobility directly, not differential mobility. However, a DMS is a very small and simple instrument compared to a traditional drift tube IMS. A solution is needed for extending the useful range of DMS spectrometry to larger molecules.

BRIEF SUMMARY OF THE INVENTION

We disclose an ion modulating differential mobility spectrometer which may include a channel through which ions in a carrier gas may pass along an axis of gas propagation. The ion modulating differential mobility spectrometer may include a differential mobility selector region located within the channel which may include an opposed pair of electrodes creates an asymmetric alternative current voltage and a variable direct current component transverse to the axis of gas propagation. The ion modulating differential mobility spectrometer may include an ion modulator region within the channel. The ion modulator region may include a longitudinal alternating current electric field along the axis of gas propagation and the longitudinal alternating current electric field may include a modulation period. The modulation period may be equal to a transit time of the carrier gas through the ion modulator region. Alternatively, the modulation period may be inversely proportional to a transit time of the carrier gas through the ion modulator region. The ion modulating differential mobility spectrometer may include an ion detector disposed in the channel.

The longitudinal alternating current field may cause ions to bunch by alternately pushing and pulling ions as they pass through the modulator. High mobility ions bunch more readily and produce a larger alternating current ion current modulation. Low mobility ions are more difficult to bunch and thus produce a smaller alternating current ion current modulation relative to the direct current which is the ion concentration. Thus, the mobility (or average mobility) of the differential mobility spectrometer output may be measured by comparing the ratio of the alternating current to the direct current.

BRIEF DESCRIPTION OF THE DRAWINGS

FIG. 5A a schematic drawing of a front view of an embodiment of the disclosed ion modulating differential mobility spectrometer.

FIG. 5B is a schematic cross-sectional view of the instrument of FIG. 5A taken through a horizontal plane extending through the axis of gas propagation.

FIG. 5C is a schematic cross-sectional view of the instrument of FIGS. 5A and 5B taken through a vertical (top-bottom) longitudinal plane extending through the center of the instrument.

DETAILED DESCRIPTION OF THE INVENTION

Figure 1:
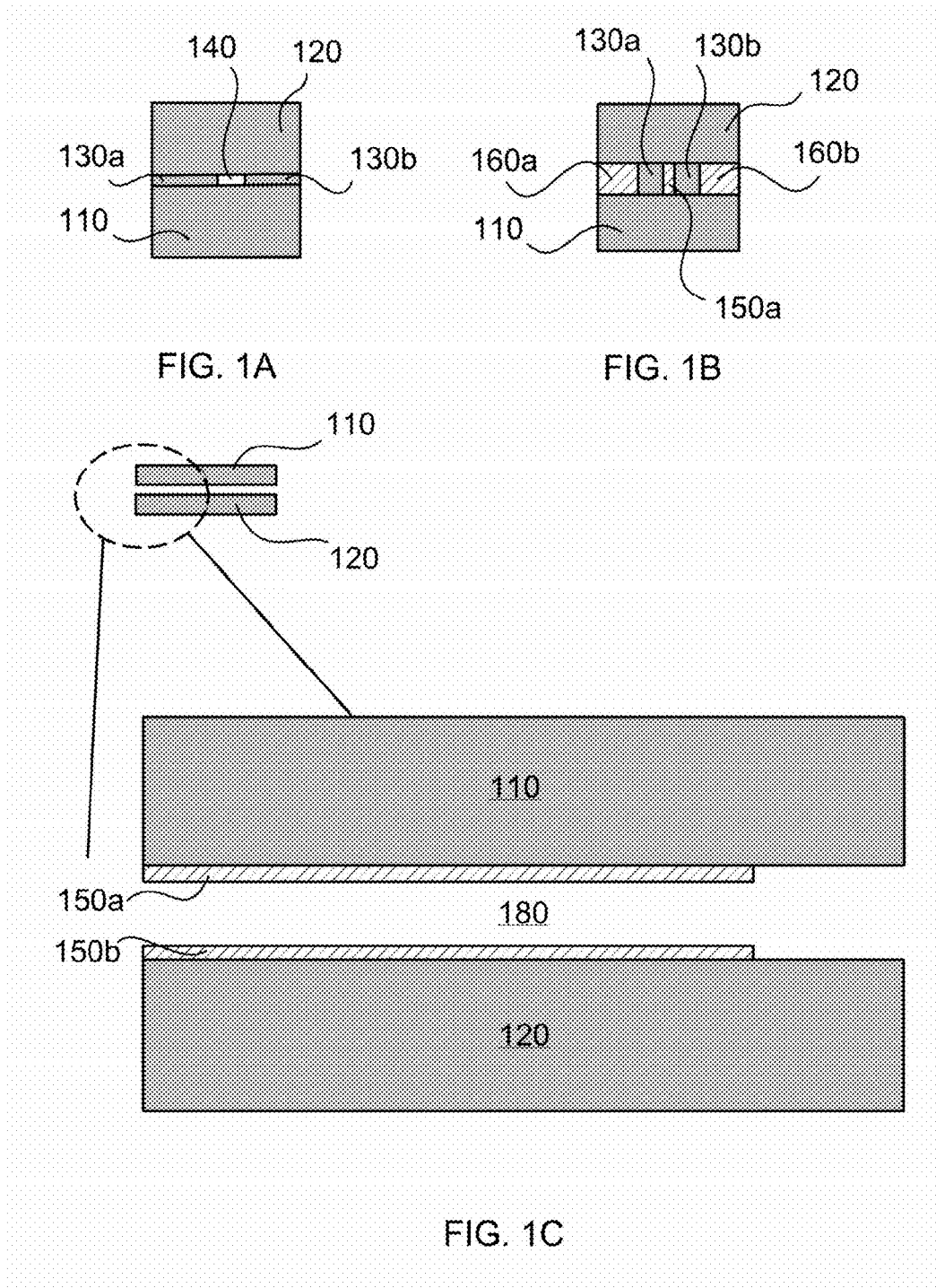
FIG. 1A is a schematic drawing of a front view of an embodiment of the disclosed ion modulating differential mobility spectrometer.
FIG. 1B is a schematic cross-sectional view of an embodiment of the disclosed ion modulating differential mobility spectrometer taken through a horizontal plane extending through the instrument of FIG. 1A along the axis of gas propagation.
FIG. 1C is a schematic cross-sectional view of an embodiment of the disclosed ion modulating differential mobility spectrometer taken through a vertical (top-bottom) longitudinal plane extending through the center of the instrument of FIGS. 1A and 1B.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose an ion modulating differential mobility spectrometer for measuring the linear mobility of a selected differential mobility. For instance, ions first pass through a differential mobility spectrometer (hereinafter, "DMS") which selects ions with low or zero differential mobility. Significantly, this step may remove reactant ions, for example, charged water complexes, leaving only large ions and their adducted molecules. Ions may pass from the DMS through an ion modulator which applies a longitudinal alternating current (hereinafter, "AC") field. The longitudinal AC field may cause ions to bunch by alternately pushing and pulling ions as they pass through the modulator. High mobility ions bunch more readily and produce a larger AC ion current modulation. Low mobility ions are more difficult to bunch and thus produce a smaller AC ion current modulation relative to the direct current (hereinafter, "DC") which is the ion concentration. Thus, the mobility (or average mobility) of the DMS output may be measured by comparing the AC/DC ratio.

Others have used DMS and ion modulators to prepare ion pulses for time of flight spectrometers (US20160071714 A1). However, such devices operate in a field regime where ion flow is dominated by the applied field and ions are bunched regardless of their mobility. Nothing is disclosed about timing the AC field of an electrode region to be synchronous with the transit time of ions moving in a stream of air or carrier gas. Rather, the disclosed ion modulating differential mobility spectrometer relies on an asymmetric field to drive ions forward.

The disclosed ion modulating differential mobility spectrometer requires no asymmetric field. A pure sinusoid waveform or other AC waveform is suitable. The more ground and AC electrode pairs are used in sequence, the lower the necessary voltage. Therefore, repeated ion bunching produces results which are equivalent to using a higher voltage. The ion modulator region may be divided into two sub-regions with opposed longitudinal electric fields which alternately point toward a center electrode and away from the center electrode when the central point is driven by an AC field. The ion modulating region may include additional repetitions of the opposed regions along the channel.

The operation is linear, and limited by diffusion and space charge effects. The time resolution with which the modulation may be detected is limited by the size of the detector electrodes and thickness of the stream of ions (i.e. the maximum ion transverse diffusion distance to electrode). Larger electrodes and channels will result in less time resolution. Detector electrodes operating at higher voltages may obtain higher resolution at the cost of higher background current and 1/f noise.

There are two regimes of operation: linear regime and nonlinear regime. In the low field linear regime, a sinusoidal field generates a sinusoidal modulation of the ion current. In the nonlinear regime ions are pressed into dense spikes. Either the linear field region or nonlinear field region may be used, or used alternately. Because this technique in the linear range measures the average mobility, if there is more than one analyte present, it is not distinguished. However, in the nonlinear regime, the waveforms from ions of differing mobility have some functional orthogonality and the presence of multiple species can be observed. Namely, where one ion is bunched tightly in a spike there may be few ions between the spikes. But where a low mobility ion is present, there is a higher-than-expected ion concentration in the rarefaction between spikes.

Multivariate analysis may be used to estimate the several values of mobility present. Note that without the prefiltering of the DMS, the resulting waveform could be dominated by the reactant ion peak and the modulation of bulkier ion complexes would be less observable.

Another application of the disclosed ion modulator is to change the ion concentration. It is well known that the ion mobility spectrum is affected by the concentration of the ion and the concentration of the reactant ion (e.g. water). At low concentrations of analyte, monomers are principally observed. At high concentrations, increasing amounts of dimer are observed. This changing spectrum as a function of intensity may complicate analysis and quantitation. By placing an ion modulator (ion buncher) in front of a DMS, regions of high and low ion concentration may be generated. By time resolving the CV scan from the high regions and low regions and/or intermediate regions, many scans of varied concentration may be obtained simultaneously without changing the concentration of ion input to the system. Therefore, the evolution of the monomer/dimer ratios vs. concentrations may be observed and used as a method of identification, or to optimized operation conditions.

In another example, an ion may saturate a detector. The disclosed modulation scheme may provide a means to measure the ion concentration in time over a wider dynamic range without altering the system operating parameters.

Each of these applications are of potential benefit for material identification and on-line monitoring applications.

In general, an ion modulator may be used before or after a DMS or between tandem DMS sections. In an example, the ion modulator may be used before a DMS. The reactant ion may have a high mobility and peak at the center of the bunch, creating regions of high and low reactant ion concentration. If negative and positive reactant ions are present, which is usually the case for water, the negative reactant ion and positive reactant ion clusters bunch out of phase. The negative reactant ion bunching peak may occur at the rarefaction of the positive reactant ion bunching peak and vice versa. The probability of neutralization of ions by collisions of positive and negative ion clusters may also be reduced by spatial separation of ion types.

Traditional ion modulators operate with asymmetric AC fields and use the electric field to move ions. Therefore, they can only be used with one polarity of ion. The other polarity is moved in the opposite (i.e. not intended) direction. Conversely, in the disclosed ion modulating differential mobility spectrometer, ion motion may be controlled by the flow rate of a carrier gas so both polarities of ions may be both bunched and transported.

Some embodiments, the distance between the ground and signal electrodes in the ion modulator may be larger than the thickness of the dielectric spacer. In an example, the spacer is between approximately 0.25 mm to approximately 1 mm thick and the longitudinal distance from the ground to the AC electrode is between approximately 2.5 to approximately 10 mm. In another example, the channel depth is between approximately 0.25 mm to approximately 1 mm. In another example, the channel width is between approximately 2 mm to approximately 8 mm. In another example, the spacer is approximately 0.5 mm, the channel width is approximately 4 mm, the AC to ground electrode distance is approximately 0.5 mm, and the air flow velocity is approximately 300 cm/s. The transit distance from ground through the AC field region to ground is 1 cm, so the transit time is 1/300 s. The AC frequency may therefore be approximately 300 Hz.

An advantage of modulating the ion current is improved detection. Noise at low frequencies tends to be larger, so-called 1/f noise. By modulating the ions, the signal may be moved to a higher (e.g hundreds of hertz) frequency. Demodulation may be accomplished by modulating the detector voltage, or by holding the detector voltage constant and demodulating detected current with a mixer and low pass filter. DC changes in background current, which is a source of drift, is eliminated while the noise bandwidth may be arbitrarily narrowed by the selection of the band pass filter. Because the bunching phase is known and/or can be controlled, a quadrature mixer is not needed. Alternatively, a phase moduation on the mixer may be used to close loop control the modulator frequency or gas flow speed to keep modulation period and modulator transit time in-phase. Alternatively, the modulation period may be inversely proportional to a transit time of the carrier gas through the ion modulator region.

In some embodiments, the ion modulating differential mobility spectrometer may include a channel through which ions in a carrier gas may be passed along an axis of gas propagation. The ion modulating differential mobility spectrometer may further include a differential mobility selector region within the channel which may include multiple pairs of electrodes. These pairs of electrodes may provide an asymmetric AC voltage and a variable DC component which may be transverse to the axis of gas propagation. The ion modulating differential mobility spectrometer may include an ion modulator region disposed within the channel. The ion modulator region may include a longitudinal AC electric field along the axis of gas propagation. In some embodiments, the ion modulator region comprises a length of between approximately 5 mm to approximately 25 mm. The longitudinal AC electric field may include a modulation period which may be equal to a transit time of the carrier gas through the ion modulator region. An ion detector may also be disposed within the channel.

The ion modulator region may include multiple pairs of ground electrodes which may define a gap or slot along the axis of gas propagation. The gap or slot may define the ion modulator region. The ion modulator region may further include a drive electrode, which may be positioned within the gap or slot. AC voltage may be applied to generate the longitudinal AC electric field. Other embodiments may include multiple drive electrodes, each separated by a counting number of transit times.

In some embodiments, the ion modulator region may be positioned further along the axis of gas propagation than the differential mobility selector region. Furthermore, the ion detector may be positioned further along the axis of gas propagation than the ion modulator region.

In some embodiments, the differential mobility sector region and ion modulator region may include planar electrodes adhered to a pair of dielectric substrates. The dielectric substrates may be separated by a dielectric space with a gap or slot running through the dielectric spacer. The gap or slot may define the channel through which gas and ions travel. In some embodiments, the ion detector may include a planar electrode.

In some embodiments, the differential mobility sector region, the ion modulator region, and the ion detector may be fabricated on a single dielectric substrate. Alternatively, the differential mobility sector region, the ion modulator region, and the ion detector may be fabricated on different dielectric substrates.

In some embodiments, the channel may include an ion interaction region between the ion modulator region and the ion detector. The ion detector may include a demodulator which may demodulate ion current at the modulation period.

The ion modulating differential mobility spectrometer may include a controller. The controller may adjust the transit time or the modulation period based on a detected modulation current magnitude. The controller may adjust the longitudinal AC electric field based on a detected modulation current magnitude. Furthermore, the controller may scan the variable DC component of the differential mobility selector through a series of direct current levels. Alternatively, the modulation period may be inversely proportional to a transit time of the carrier gas through the ion modulator region.

The ion modulating differential mobility spectrometer may include a recorder, which may record a time-resolved measurement of the detected modulation current magnitude.

Some embodiments may include a boxcar averager which may obtain an average of a time-resolved measurement of the detected modulation current magnitude. Some embodiments may include a controller, a recorder, and a boxcar averager.

Some embodiments may include an analyzer which may estimate one of more ion mobilities from the time-resolved of the detected modulation current magnitude.

Referring now to the drawings, FIG. 1A is a schematic drawing of a front view of an embodiment of the disclosed ion modulating differential mobility spectrometer. Top dielectric substrate 110 and bottom dielectric substrate 120 are shown. Two sides of a dielectric spacers 130a and 130b are shown between top dielectric substrate 110 and bottom dielectric substrate 120. Channel entrance aperture 140 leads into a channel which is defined by a space that runs through the dielectric spacer.

FIG. 1B illustrates a schematic drawing of a top cross-sectional view of the ion modulating differential mobility spectrometer of FIG. 1A. The cross-section is taken through a plan that runs along the axis of gas propagation which begins at channel entrance aperture 140 and runs longitudinally toward the opposite end of the instrument. This direction is left to right in the drawing. The top sections of the two dielectric substrates 110 and 120 are shown. An AC voltage electrode 150a and two ground electrodes 160a and 160b are adjacent to the inner surface of the dielectric substrates 110 and 120. Ground electrodes 160a and 160b are shown flanking AC voltage electrode 150a. Sections between electrodes show sections of dielectric spacers 130a.

The top left of FIG. 1C shows a schematic cross-sectional view of the ion modulating differential mobility spectrometer of FIGS. 1A and 1B taken through a plane that runs vertically through channel 180 along the axis of gas propagation. This view shows dielectric substrates 110 and 120. FIG. 1C further shows an expanded view of the left end of the ion modulator nearest channel entrance aperture 140. In the expanded view, AC voltage electrodes 150a and 150b are shown adhered to dielectric substrates 110 and 120. Channel 180 runs between AC voltage electrodes 150a and 150b.

Figure 2:
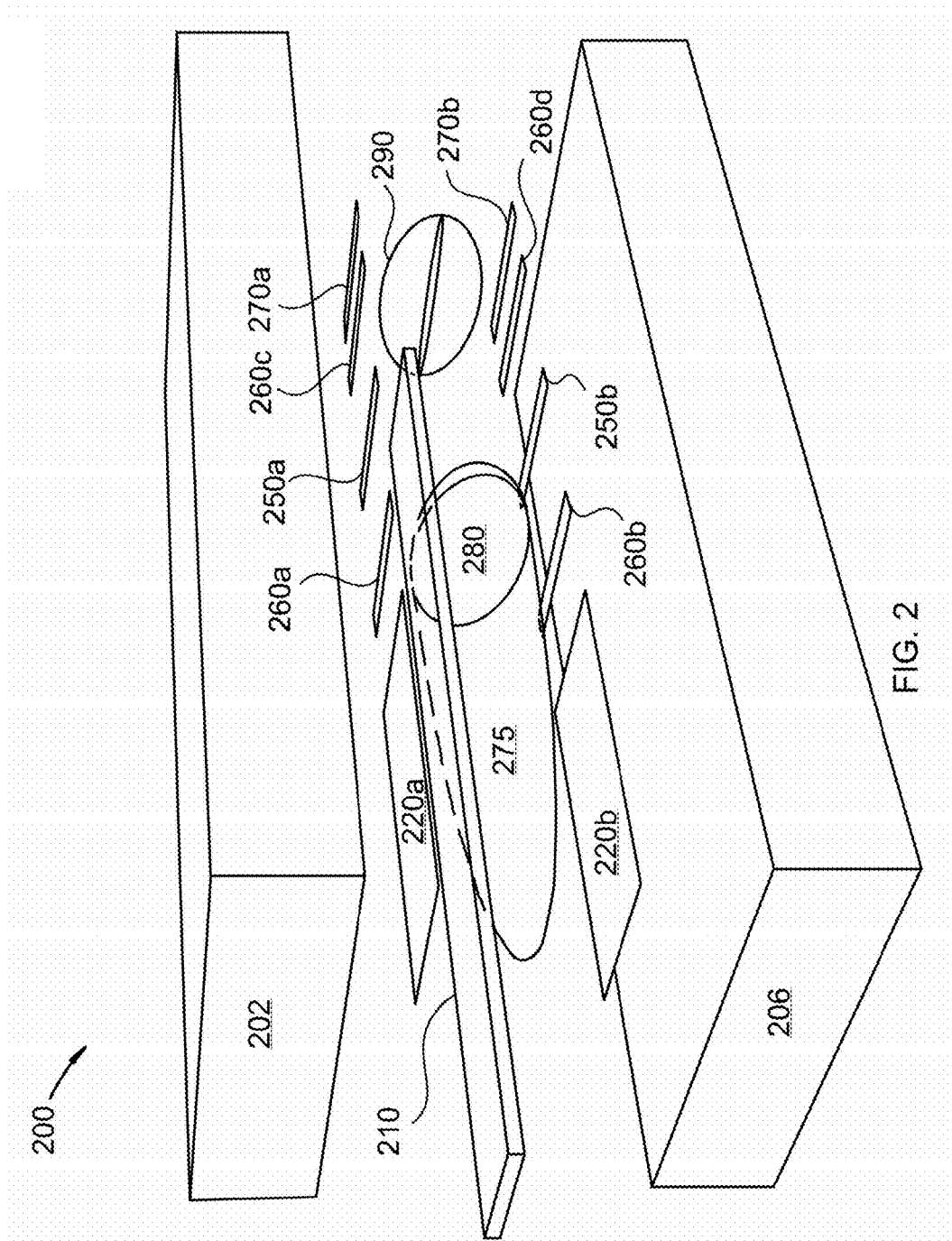
FIG. 2 is an exploded view of an embodiment of the disclosed ion modulating differential mobility spectrometer.

FIG. 2 is an exploded view of ion modulating differential mobility spectrometer 200, an embodiment of the disclosed invention. Dielectric substrates 202 and 206 are shown on either side of dielectric spacer 210. Dielectric spacer 210 includes a longitudinal slot which defines the channel through which gas and ions travel along the axis of gas propagation. For simplicity, only the top section of dielectric spacer 210 is shown. A plurality of electrodes is adhered to the inner sides of dielectric substrates 202 and 206. Nearest the viewer, and nearest the beginning of the axis of gas propagation, are two DMS HV electrodes 220a and 220b. Ion bolus 275 is shown between DMS HV electrodes 220a and 220b. Ground electrodes 260a and 260b are shown further along the axis of gas propagation with a front of bunched ions 280 between them on the leading end of ion bolus 275. AC voltage electrodes 250a and 250b are shown further along the axis of gas propagation followed by two more ground electrodes, labeled ground electrodes 260c and 260d. Detector electrodes 270a and 270b are shown at the far end of the axis of gas propagation. A bolus of bunched ions 290 is shown between detector electrodes 270a and 270b.

Figure 3:
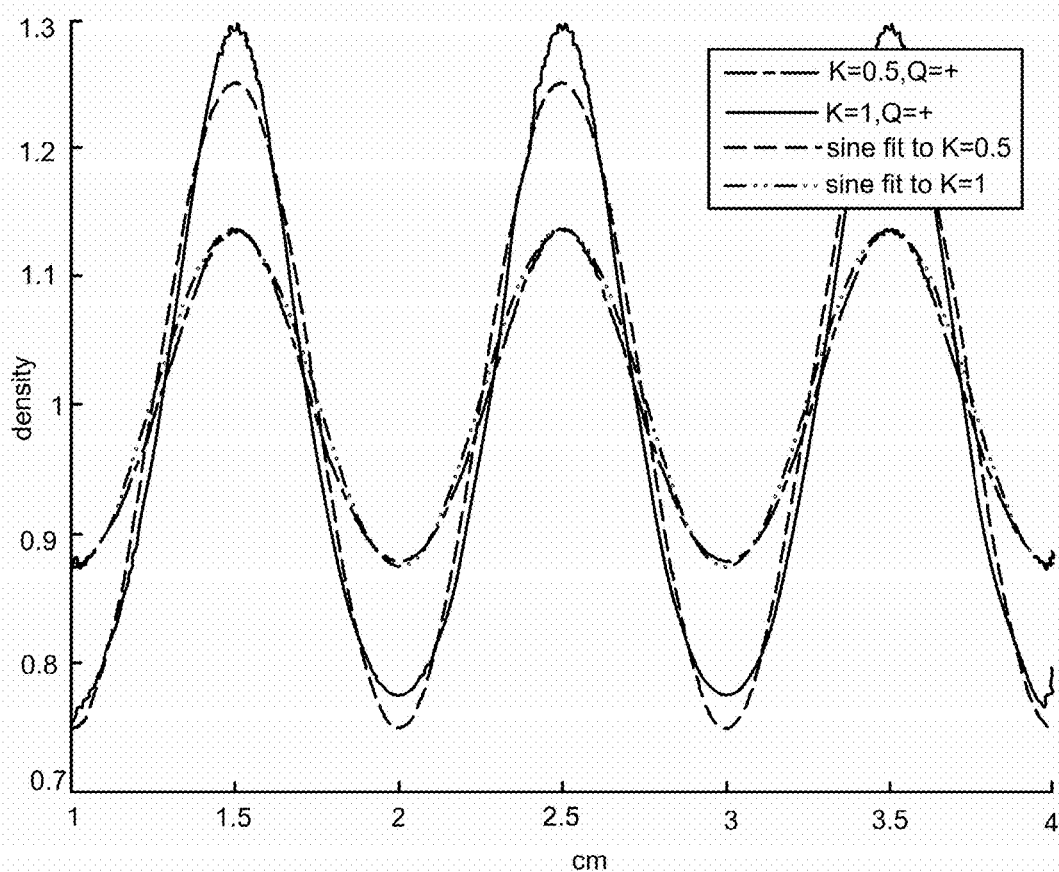
FIG. 3 is a graph illustrating a simulation of coherent modulation of ions of differing mobility in and near the linear regime.

FIG. 3 is a graph illustrating a simulation of coherent modulation (modulation frequency matched to transit time) of ions of differing mobility showing increasing amplitudes of modulation with increasing mobility in and near the linear regime. The graph illustrates that, in the low field linear regime, a sinusoidal field generates a sinusoidal modulation of the ion current.

Figure 4A:
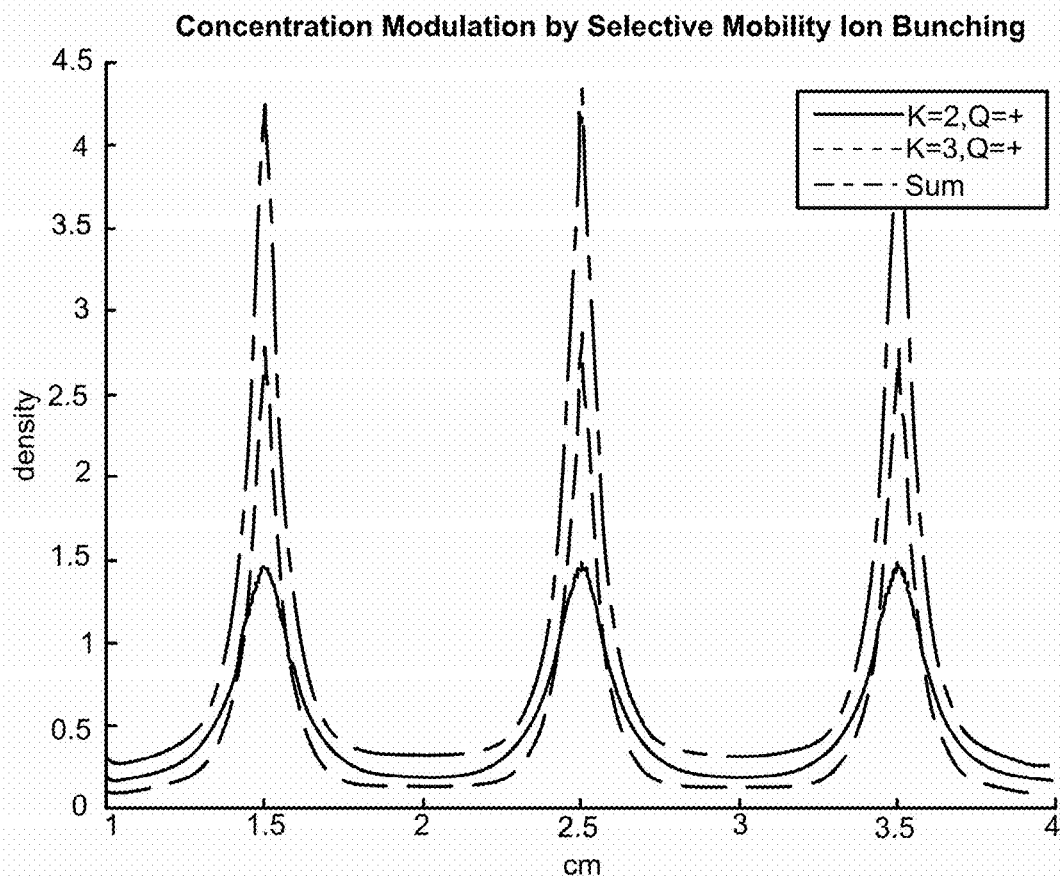
FIG. 4A is a graph illustrating a simulation of coherent modulation of two analytes of differing mobility and the resulting sum signal observed on an ideal detector.

FIG. 4A is a graph illustrating a simulation of coherent modulation (modulation frequency matched to transit time) of two analytes, one with reduced mobility of 2 $cm^2/(V*s)$ and one with mobility of 3 $cm^2/(V*s)$ and the resulting sum signal observed on an ideal detector. As shown in the graph of FIG. 4A, nonlinear regime ions are pressed into dense spikes in contrast to the sinusoidal appearance of the graph of FIG. 3.

Figure 4B:
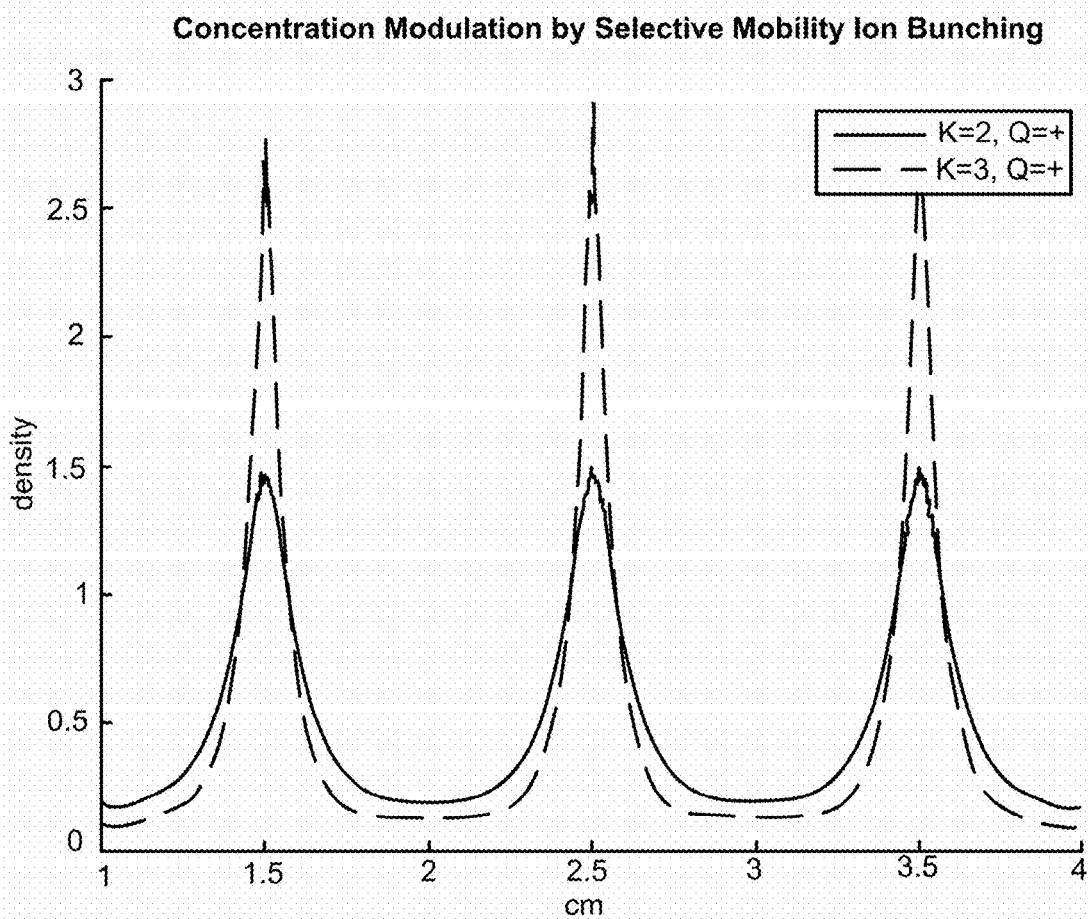
FIG. 4B is a graph illustrating ions of different mobility in the nonlinear regime showing selective bunching.

FIG. 4B is a graph showing a simulation of ions of different mobility in the nonlinear regime. The graph shows selective bunching which leads to a concentration ratio modulation. In the rarefaction, the low mobility to high mobility ion concentration ratio is approximately 2. In the compression peak the concentration ratio inverts with the high mobility analyte having both a higher concentration and a higher ratio of concentration to the low mobility analyte.

FIGS. 5A, 5B, and 5C are schematic drawings of different views of an embodiment of the ion modulating differential mobility spectrometer. FIG. 5A is a front view of the device which resembles that of FIG. 1A. Top dielectric substrate 110 and bottom dielectric substrate 120 are shown. Two sides of a dielectric spacers 130a and 130b are shown between top dielectric substrate 110 and bottom dielectric substrate 120. Channel entrance aperture 140 leads into a channel which is defined by a space that runs through the dielectric spacer.

FIG. 5B illustrates a schematic drawing of a top cross-sectional view of the ion modulating differential mobility spectrometer of FIG. 5A. The cross-section is taken through a plane that runs along the axis of gas propagation which begins at channel entrance aperture 140 and runs longitudinally toward the opposite end of the instrument (left to right on the drawing). Electrodes are shown as hatched regions and solid colored regions between electrodes represent sections of the dielectric spacer which is not adjacent to an electrode. The embodiment of FIG. 5B includes multiple sections which contribute to ion bunching and separation according to size. Beginning at the most proximal end of the axis of gas propagation, these include ion modulator 505, interaction region 520, differential mobility spectrometer 510, ion modulator 517, interaction region 525, differential mobility spectrometer 515, ion modulator 519, and detector 570. Ion modulator 505 may be used to generate a gradient of reactant ion versus analyte density. Analyte ion clusters may evolve via collisions within interaction regions 520 and 525. Differential mobility spectrometer 510 may select a differential ion mobility range of interest. Ion modulator 517 may generate an analyte concentration gradient with the excess reactant ion removed by differential mobility spectrometer 510. Differential mobility spectrometer 515 may select a final ion mobility range of interest for observing changes to the ion spectrum in interaction region 525 due to modulated concentrations. Detector 570 may measure positive and negative ion concentrations.

As a practical consideration, the operation of ion modulators is approximately linear, so tandem bunchers allow a smaller voltage to be used to achieve a similar level of ion bunching, limited by diffusion effects and field irregularities.

Figure 6:
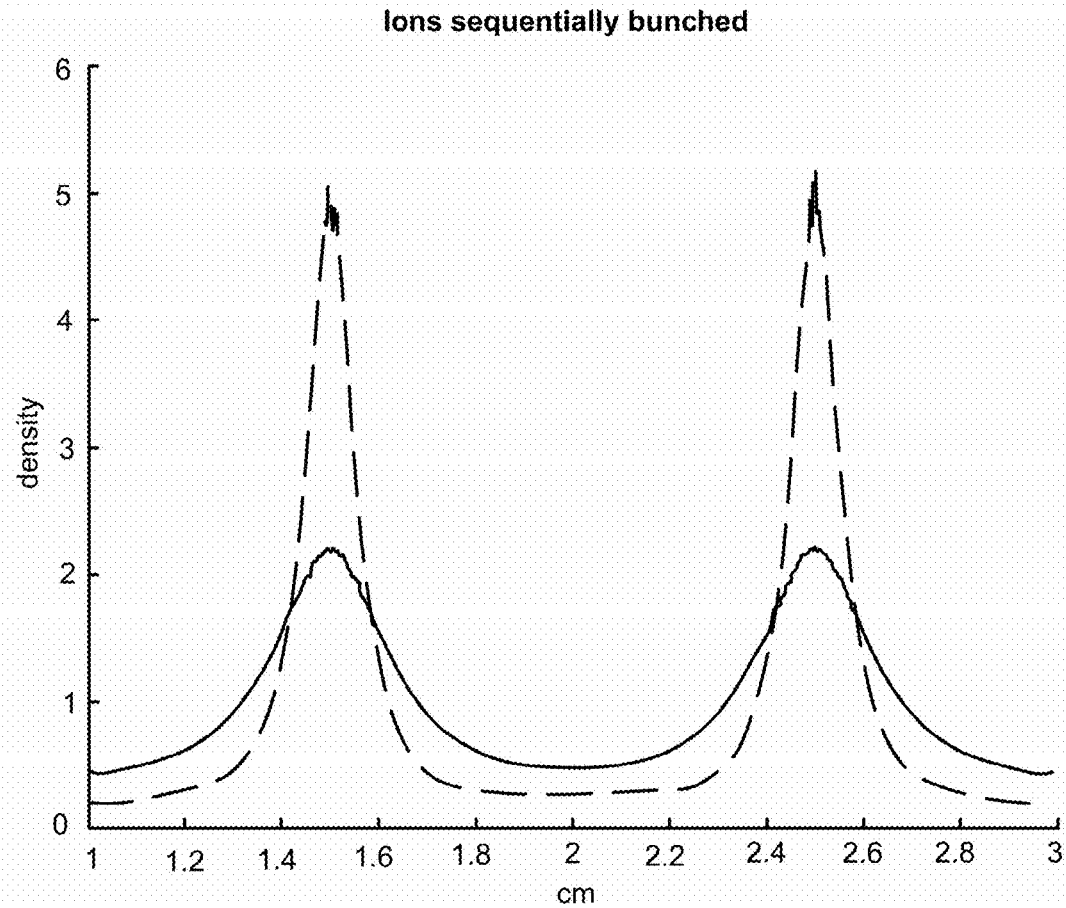
FIG. 6 is a graph illustrating a simulation of ions bunching after going through an instrument including either one ion modulation regions or two modulation regions.

FIG. 6 is a graph illustrating a comparison of ion bunching using one ion modulator (solid line) and using two ion modulators (dashed line). The dashed line may be produced by the embodiment of FIGS. 5A-C. Because the phase of the modulator is definite and matched to the ion flow speed, the position of ion peaks is definite. A second modulator can be used out of phase to de-bunch the ions, if desired, for obtaining an unmodulated output, to the extent that diffusion and space charge effects are negligible (independent ion approximation).

Figure 7:
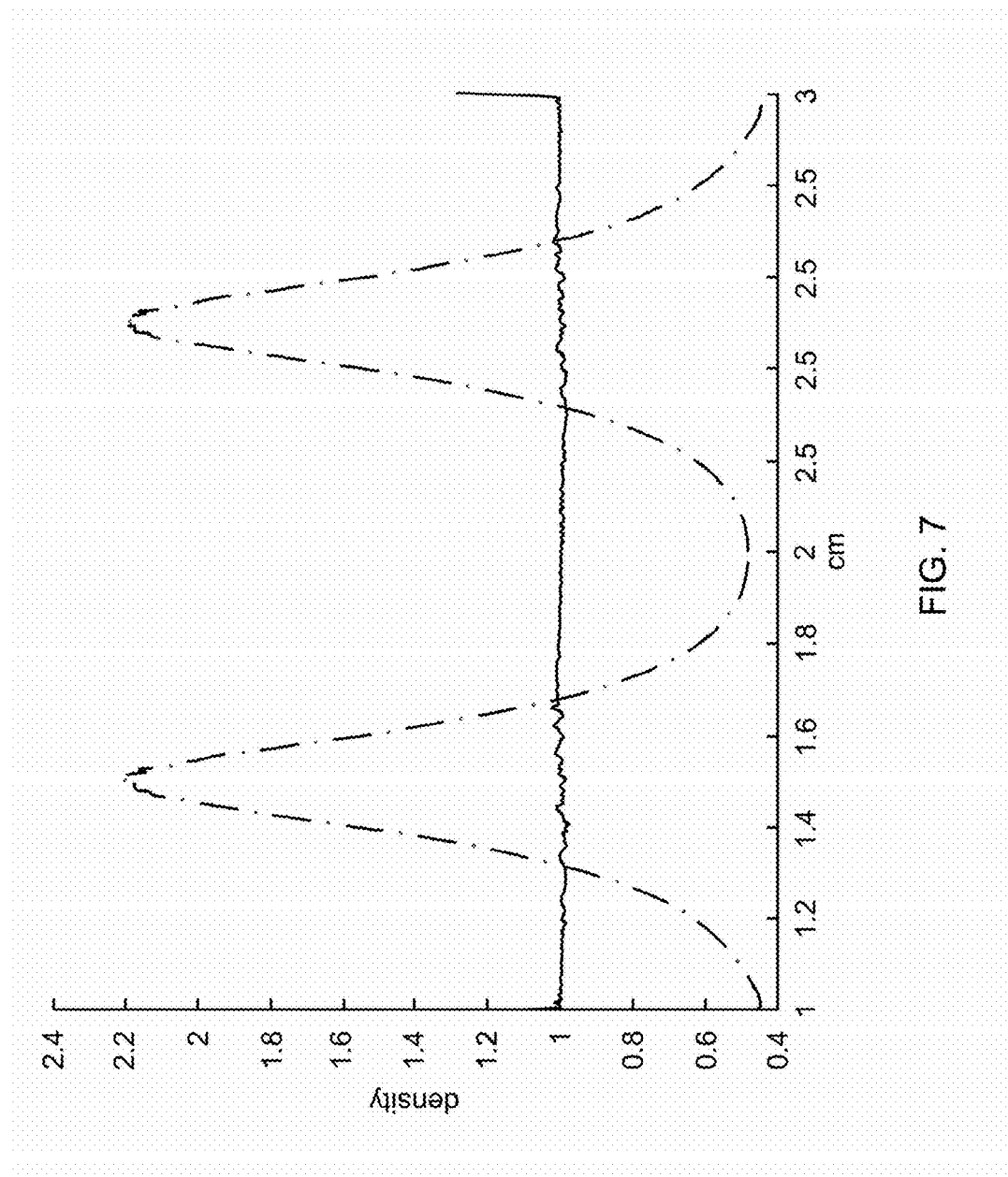
FIG. 7 is graph illustrating a simulation of ions bunching or ions bunching followed by de-bunching.

FIG. 7 is a graph showing a simulated separation using a first ion modulator compared to using a first and a second ion modulator. The dashed/dotted line shows ion bunching. The solid line shows ion bunching followed by debunching.

Figure 8:
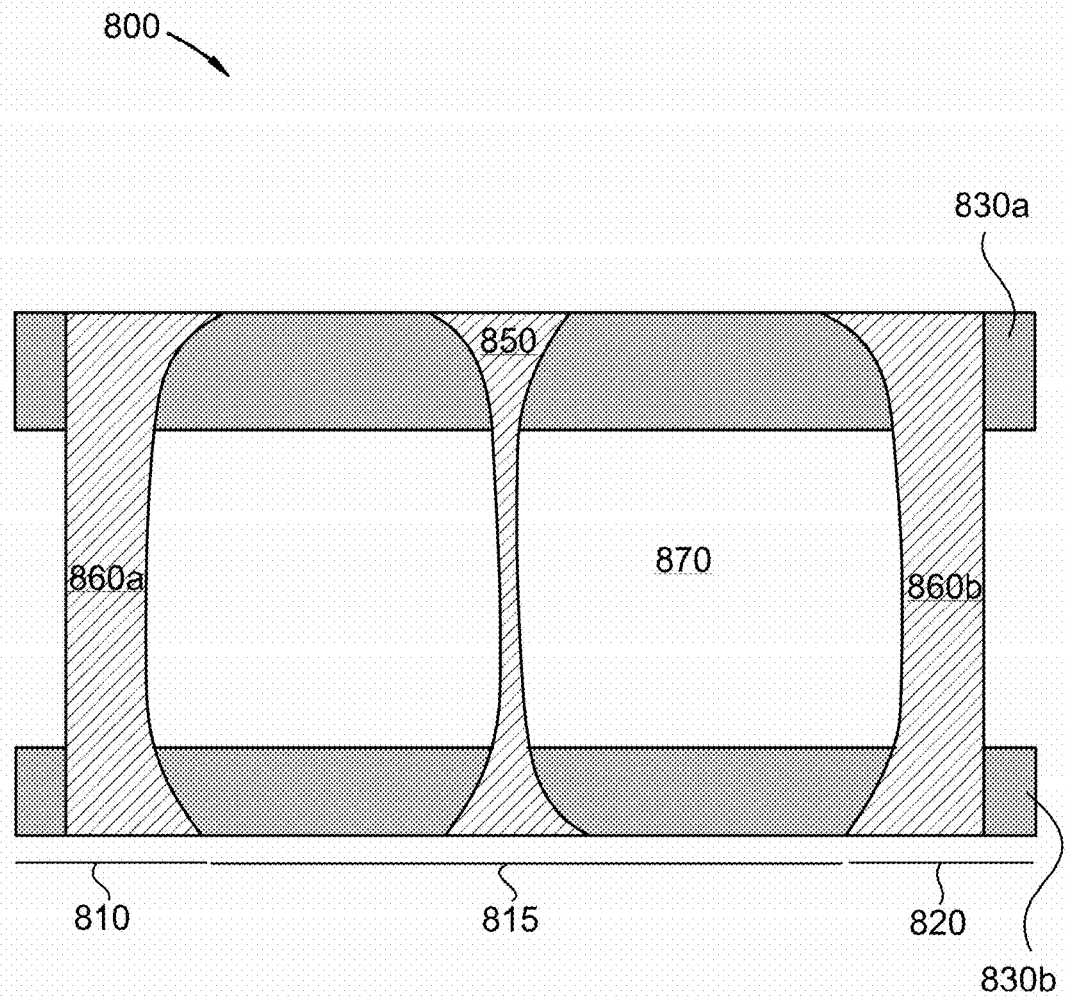
FIG. 8 is an illustration of an electrode according to an embodiment of the disclosed instrument which is designed to push electric fields out of the dielectric space.

FIG. 8 is a schematic drawing of ion modulating differential mobility spectrometer 800 which includes electrodes designed to push electric fields out of the dielectric space to obtain a more longitudinal electric field in the channel. The drawing is a top cross-sectional view. Sides 830a and 830b of the dielectric spacer are shown which define channel 870. Shaped electrodes are shown along the dielectric spacer. Specifically, AC voltage electrode 580 is concave on both sides. Ground electrodes 860a and 860b are concave on the sides facing AC voltage electrode 850. Electric field region 815 is generated between ground electrodes 860a and 860b. The electric field region 815 has two regions of opposed electric field with one region between ground electrode 860a and the AC voltage electrode, and the other region between ground electrode 860b and the AC voltage electrode. The electric field in these regions alternately points from the ground electrodes 860a and 860b to the AC voltage electrode 580 and vice-versa when the AC voltage electrode is driven with an AC voltage. Regions 810 and 820 ideally have no electric field or a small electric field due to the shielding provided by the ground electrodes.

Uniform axial fields are desirable for bunching ions distributed through the entire sample cross sectional area. In a planar design, two plates with metal traces for forming the electrodes are spaced by a dielectric. The dielectric tends to attract electric field. To compensate the ground and signal electrode shapes can be altered to focus the fields to achieve a better longitudinal field.

Figure 9A:
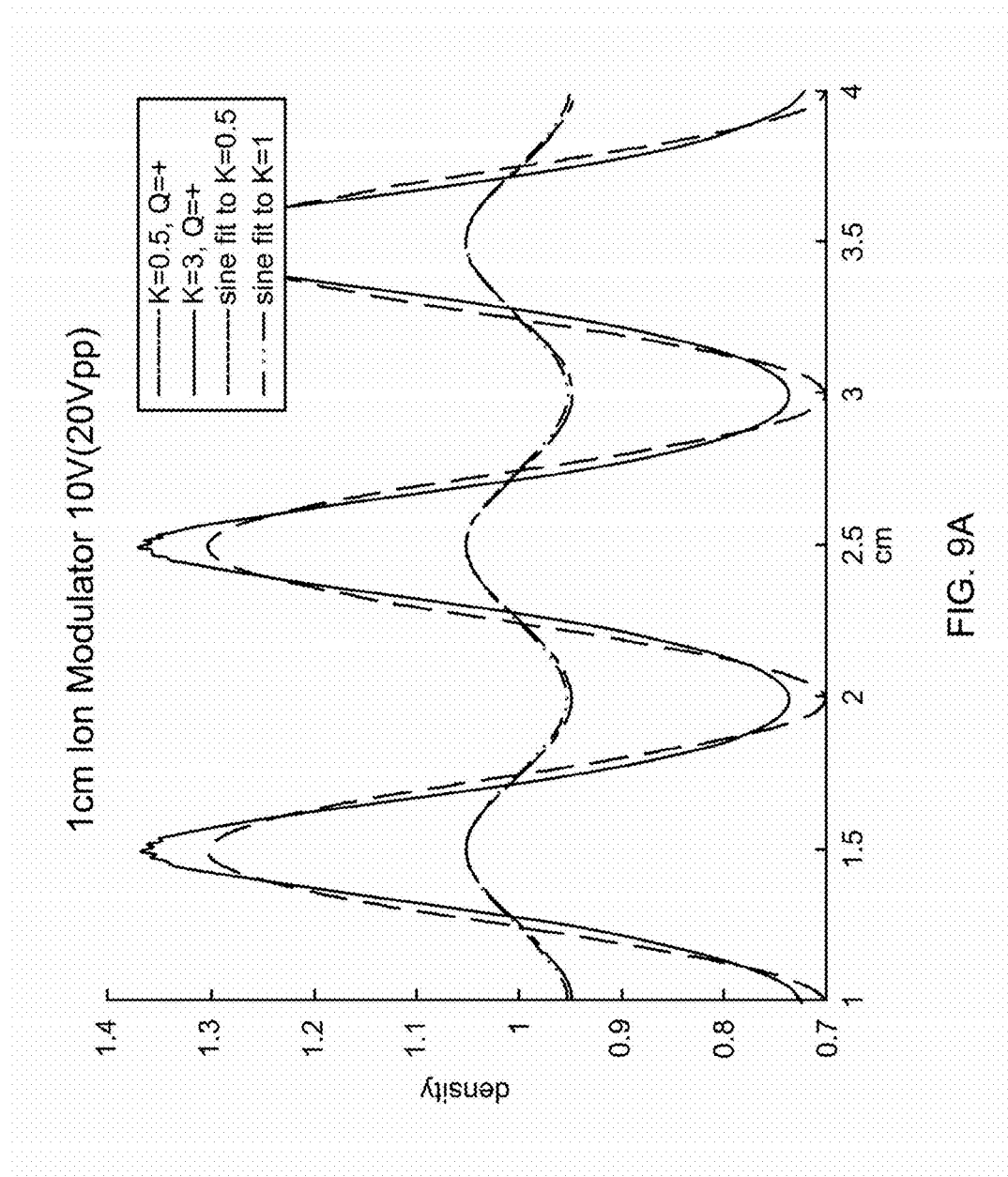
FIGS. 9A and 9B are graphs illustrating illustrate two simulated separations conducted using an embodiment of the disclosed instrument using voltages of either 10 V or 50 V.
Figure 9B:
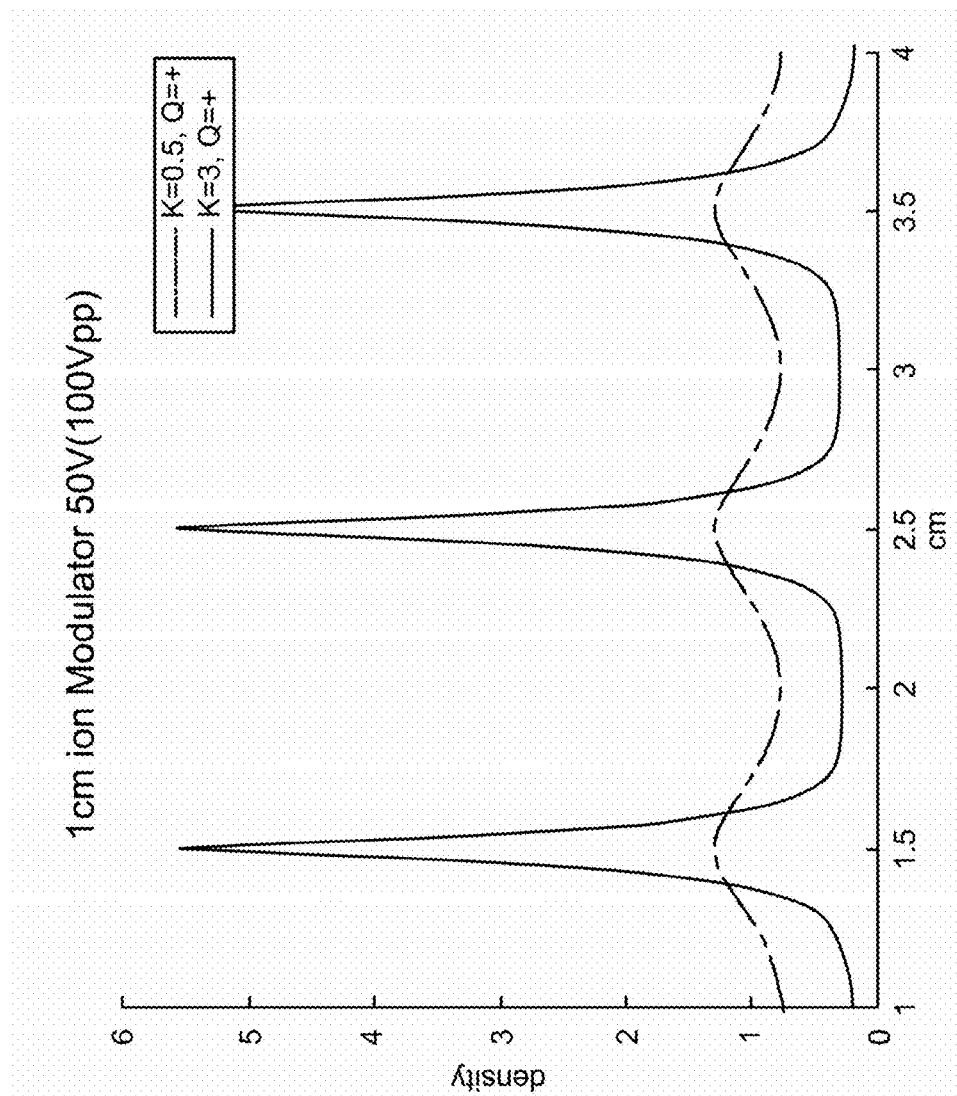

FIGS. 9A and 9B are graphs showing simulations of an embodiment of the disclosed ion modulating differential mobility spectrometer. FIG. 9A shows a simulation of ion density vs. position along the axis of propagation in the channel after passing through a 1 cm ion modulating differential mobility spectrometer at 10 V (20 Vpp). FIG. 9B shows a simulation of ion density for a 1 cm ion modulating differential mobility spectrometer at 50 V (100 Vpp). In these examples which utilize a single AC electrode, AC amplitude of 10 V produces bunching in the linear regime and AC amplitude of 50V produces bunching in the nonlinear regime, for typical ranges of volatile ion reduced mobility of 0.5-3 cm^2/(V*s). It should be clarified that the bunching is a linear operation in the sense that the operator is linear in the independent ion approximation (bunching is additive and can be undone), although it results in spiked profiles which are not linear combinations of sine waves. This is what is meant by the term "nonlinear regime".

While specific embodiments have been described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. An ion modulating differential mobility spectrometer comprising:
   a. a channel through which ions in a carrier gas are passed, wherein the channel comprises an axis of gas propagation;
   b. a differential mobility selector region located within the channel, the differential mobility sector region comprising a plurality of electrodes, wherein the plurality of electrodes provides an asymmetric alternative current voltage and a variable direct current component which is transverse to the axis of gas propagation;
   c. an ion modulator region disposed within the channel, the ion modulator region comprising a longitudinal alternating current electric field along the axis of gas propagation, wherein the longitudinal alternating current electric field comprises a modulation period, wherein the modulation period is equal to a transit time of the carrier gas through the ion modulator region; and
   d. an ion detector disposed in the channel.

2. The ion modulating differential mobility spectrometer of claim 1, wherein the ion modulator region is positioned further along the axis of gas propagation than the differential mobility selector region, and wherein the ion detector is positioned further along the axis of gas propagation than the ion modulator region.

3. The ion modulating differential mobility spectrometer of claim 1, wherein the differential mobility sector region and ion modulator region are comprised of planar electrodes on a pair of substrates, wherein the pair of substrates are separated by a dielectric spacer, and wherein the channel runs through a center of the dielectric spacer.

4. The ion modulating differential mobility spectrometer of claim 3, wherein the ion detector comprises planar electrodes.

5. The ion modulating differential mobility spectrometer of claim 1, wherein the differential mobility sector region, the ion modulator region, and the ion detector are fabricated as planar electrodes on two dielectric substrates.

6. The ion modulating differential mobility spectrometer of claim 1, wherein the channel comprises a depth of approximately 0.25 mm to approximately 1 mm.

7. The ion modulating differential mobility spectrometer of claim 1, wherein the channel comprises a width of approximately 2 mm to approximately 8 mm.

8. The ion modulating differential mobility spectrometer of claim 1, wherein the ion modulator region comprises a length of approximately 5 mm to approximately 25 mm.

9. The ion modulating differential mobility spectrometer of claim 1, wherein the ion modulator region comprises:
   a. a plurality of ground electrodes, wherein the plurality of ground electrodes defines a gap along the axis of gas propagation, and wherein the gap defines the ion modulator region; and
   b. a drive electrode, wherein the drive electrode is positioned within the gap, and wherein alternating current voltage is applied to generate the longitudinal alternating current electric field.

10. The ion modulating differential mobility spectrometer of claim 1, wherein the ion detector comprises a demodulator which demodulates ion current at the modulation period.

11. The ion modulating differential mobility spectrometer of claim 1, further comprising a controller, wherein the controller adjusts the transit time or the modulation period based on a detected modulation current magnitude.

12. The ion modulating differential mobility spectrometer of claim 1, further comprising a controller, wherein the controller adjusts the longitudinal alternating current electric field based on a detected modulation current magnitude.

13. The ion modulating differential mobility spectrometer of claim 12, further comprising a recorder, wherein the recorder records a time-resolved measurement of the detected modulation current magnitude.

14. The ion modulating differential mobility spectrometer of claim 13, further comprising a boxcar averager, wherein the boxcar averager obtains an average of a time-resolved measurement of the detected modulation current magnitude.

15. The ion modulating differential mobility spectrometer of claim 13, wherein the controller scans the variable direct current component of the differential mobility selector through a series of direct current levels.

16. The ion modulating differential mobility spectrometer of claim 15, further comprising:
   a. a recorder, and
   b. a boxcar averager, wherein the recorder records a boxcar average of the time-resolved modulated current at each direct current level.

17. The ion modulating differential mobility spectrometer of claim 13, further comprising an analyzer, wherein the analyzer estimates one of more ion mobilities from the time-resolved of the detected modulation current magnitude.

18. The ion modulating differential mobility spectrometer of claim 1, wherein the channel further comprises an ion interaction region between the ion modulator region and the ion detector.

* * * * *